United States Patent [19]

Querou

[11] 4,309,549
[45] Jan. 5, 1982

[54] BENZOXAZOLONE PREPARATION

[75] Inventor: Yvon Querou, Nanterre, France

[73] Assignee: Rhone-Poulenc Agrochimie, Lyons, France

[21] Appl. No.: 143,857

[22] Filed: Apr. 25, 1980

[30] Foreign Application Priority Data

May 8, 1979 [FR] France .................................. 79 12139

[51] Int. Cl.$^3$ .......................................... C07D 263/58
[52] U.S. Cl. .................................................. 548/221
[58] Field of Search ........................................ 548/221

[56] References Cited

U.S. PATENT DOCUMENTS 3,812,138  5/1974  Heise et al. ........................ 548/165

FOREIGN PATENT DOCUMENTS 1269067  7/1961  France .................................. 548/221
2048270  12/1980  United Kingdom ................. 548/221

OTHER PUBLICATIONS

Wagner et al., "Synthetic Organic Chemistry," (1951), pp. 665–666.

*Primary Examiner*—Anton H. Sutto
*Attorney, Agent, or Firm*—Burns, Doane, Swecker & Mathis

[57] ABSTRACT

Benzoxazolone is prepared by heating a mixture of ortho-chlorophenol and urea under superatmospheric ammonia pressure, and then continuing heating the medium of reaction, but under atmospheric pressure.

26 Claims, No Drawings

BENZOXAZOLONE PREPARATION

CROSS-REFERENCE TO RELATED APPLICATION

My copending application, Ser. No. 143,859, filed concurrently herewith, and hereby expressly incorporated by reference in its entirety and relied upon.

BACKGROUND OF THE INVENTION

1. Field of the Invention

The present invention relates to the preparation of benzoxazolone from a phenol, and, to more especially, the preparation of benzoxazolone from chlorophenol.

2. Description of the Prior Art

Benzoxazolone is a known compound having the structural formula:

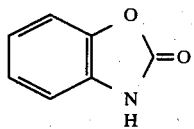

Such known compound is a useful intermediate in the synthesis of a variety of other materials, e.g., the insecticide phosalone. And benzoxazolone is ofttimes designated benzoxazolinone, in particular in the English speaking countries.

It too is known to prepare benzoxazolone by fairly diverse methods, beginning with rather exotic reactants. Compare, for example, French Pat. No. 1,269,067. Also compare U.S. Pat. No. 3,812,138.

SUMMARY OF THE INVENTION

Accordingly, a major object of the present invention is the provision of a simple and facile process for the preparation of benzoxazolone, starting with simple reactants and, more particularly, utilizing ortho-chlorophenol as the primary reactant.

Briefly, the present invention features a process for the preparation of benzoxazolone from ortho-chlorophenol, comprising, in a first step, heating a mixture of the ortho-chlorophenol and urea under positive ammonia pressure, and then, in a second distinct step, heating such reaction mixture resulting from said first step under atmospheric pressure, preferably in the presence of water.

DETAILED DESCRIPTION OF THE INVENTION

More particularly according to this invention, in a preferred embodiment the first step of the subject process is carried out in the presence of a metal catalyst; a copper-based catalyst is advantageously employed for this purpose. Exemplary of such catalysts are cuprous or cupric salts, in particular the halides, sulfates, phosphate, acetates, propionates and acetylacetonates (cuprous chloride is preferred), and also the oxides (in particular cuprous oxide), and copper metal; the catalysts comprising iron or nickel are also envisaged.

The amount of catalyst present in the reaction medium is generally between 0.5 and 20%, preferably between 2 and 10%, by weight, relative to the ortho-chlorophenol. However, while amounts of catalyst without these ranges can indeed be used, such would not constitute any significant advantage, economic or otherwise.

The first reaction step is also carried out under ammonia pressure. In other words, the subject process comprises heating a liquid reaction medium under a pressurized atmosphere which includes ammonia gas. Preferably, the $NH_3$ is added, under pressure, to the atmosphere surmounting or enveloping the reaction medium, but it is also possible to effect formation of this atmosphere under ammonia pressure by permitting the urea for the reaction mixture to decompose. The total pressure is advantageously between 1 and 60 bars (relative pressures), preferably between 3 and 40 bars. Higher pressures, e.g., ranging up to 150 bars, can also be used, but this too does not afford a great economic advantage.

The introduction of water into the reaction medium circumscribes another preferred embodiment of the invention, the effect of which, in particular, is to partially decompose the urea and thus to assist in formation of ammonia, and this can contribute to an increase in the ammonia pressure prevailing over the reaction medium. The proportion of water in the reaction medium is advantageously less than 20%, preferably less than 10% (percentages by weight, relative to the total reaction medium).

In the aforementioned atmosphere comprising ammonia and surmounting the reaction medium in the first step, the ammonia gas ($NH_3$) advantageously contributes a partial pressure of more than 50% of the total pressure, preferably of more than 90% of this pressure. Said ammonia gas is most frequently supplied from either an external feed, or is earlier introduced into the reactor, or results from decomposition of the urea, or from a combination of any two or more of the aforesaid factors.

The molar ratio of the urea employed in the reaction medium, relative to the ortho-chlorophenol, is typically between 1 and 15, preferably between 1.2 and 8.

The urea present in the reaction medium is optionally prepared, in situ, by reacting $CO_2$ with the ammonia.

The temperature of the reaction medium in the first step is advantageously between 100° and 250° C., preferably between 140° and 230° C.

The first reaction step can also be carried out in the presence of inert inorganic or organic solvents, but, generally, it is preferably carried out in bulk. Such bulk reaction mixture is typically liquid at the temperature of reaction, albeit it can indeed be non-liquid at ambient temperature.

The duration of this first reaction step can obviously vary, depending upon the operating conditions. Simple routine experiments will enable those skilled in the art to determine the optimum duration; generally, this first reaction step is continued until the ortho-chlorophenol content of the reaction admixture is no longer varying to any significant extent, or, stated differently, until the degree of conversion of the ortho-chlorophenol has essentially reached its maximum, not taking into account simple thermal and/or chemical degradation.

As heretofore indicated, the process of the invention comprises two reaction steps; in fact, these two steps are separate and distinct, in particular by reason of the fact that the first is conducted under a pressure head, while the second is simply carried out under atmospheric pressure. However, apart from this distinction, these two steps are somewhat similar from a practical point of view and same can conveniently be carried out one after the other, or sequentially, simply by means of a small change in the operating conditions, but without same being truly necessary, between the two reaction steps, e.g., to transfer the reaction medium to another reactor or to subject same to certain particular treatments. This reflects that, despite the ostensible inclusion of two distinct reaction steps, the process of the invention is indeed very simple and very convenient to carry out. This simplicity and this convenience are virtually tantamount to a process strictly comprising but a single reaction step.

The second reaction step is carried out under atmospheric pressure, preferably in a vessel open to the atmosphere. In view of the volatility of ammonia, heating under atmospheric pressure is equivalent to heating in the total or virtually total absence of ammonia. However, a small amount of ammonia can be present, especially due to the decomposition of the urea to at least some extent, but even in this case the ammonia readily evolves from the reaction medium under the influence of the heat.

The reaction temperature for the second step is typically between 80° and 220° C., preferably between 110° and 190° C.

This second reaction step, moreover, is preferably carried out in the presence of water. However, in view of the temperature and the pressure, the water tends to evaporate more or less rapidly, such that, in accordance with another embodiment of the invention, liquid water is continuously fed into the reaction medium and, if appropriate, the steam leaving the reaction medium is recovered and condensed. In accordance with these procedures, water is advantageously fed into the reaction medium at a rate per hour which is less than 20% by weight of the reaction medium. Upon completion of the reaction, the benzoxazoline is isolated and recovered by any means itself known to the art. According to a preferred and quite advantageous operational technique, the benzoxazolone is precipitated with water which may itself be acidified; the benzoxazolone can be purified by any known means, e.g., by recrystallization or by washing with an organic solvent.

The process of the invention is especially worthwhile because of the good results obtained, both as regards the degree of conversion of the ortho-chlorophenol and the yields of benzoxazolone, and also in respect of the simplicity and the convenience with which the process is carried out.

In order to further illustrate the present invention and the advantages thereof, the following specific examples are given, it being understood that same are intended only as illustrative and in nowise limitative. In the examples which follow, DC denotes the degree of conversion of the ortho-chlorophenol and Y denotes the yield of benzoxazolone, relative to the ortho-chlorophenol converted.

EXAMPLE 1

Ortho-chlorophenol (257 g), urea (300 g) and $Cu_2Cl_2$ (19.8 g) were supplied to a 1.5 liter stainless steel autoclave equipped with stirring means.

The autoclave was purged with ammonia. The reaction mixture was heated to 170° C. and then placed under a head of constant pressure of 22 bars of ammonia (relative pressure). Heating was continued for 6 hours, during which time $NH_3$ (69 g) was consumed. The autoclave was cooled to 110° C., degassed and fitted with a descending condenser connected to the reactor via a bent tube. The temperature was raised to 125° C.; the pressure being equal to atmospheric pressure because the reaction medium was exposed to the ambient atmosphere by means of the descending condenser. Water was added to the reaction medium at a rate of 65 cc/hour, while at the same time heating distillation were conducted for two hours at 140° C., and then for two hours at 150° C. The autoclave was cooled to 120° C. and water (0.8 liter) was added. The benzoxazolone precipitated; the reaction medium was stirred overnight and an aqueous solution of sulfuric acid containing 3 mols/liter (0.15 liter was then added. The benzoxazolone was filtered off and then washed and recrystallized. The benzoxazolone was thus obtained in a Y of 74.5% and a DC of 94.5%.

EXAMPLE 2

Example 1 was repeated, but with 9.9 g of $Cu_2Cl_2$ (instead of 19.8 g) being utilized. 60 g of $NH_3$ were consumed. The benzoxazolone was obtained in a Y of 79.5% and a DC of 84.5%.

EXAMPLE 3

Example 1 was repeated, but the following amounts of reactants were utilized: ortho-chlorophenol (385.5 g), urea (270 g) and $Cu_2Cl_2$ (29.7 g).

93 g of $NH_3$ were consumed during the reaction. The benzoxazolone was obtained in a Y of 67% and a DC of 93.5%.

EXAMPLE 4

Ortho-chlorophenol (257 g), urea (300 g), $Cu_2Cl_2$ (19.8 g) and $NH_3$ (68.1 g) were introduced into a 1.5 liter autoclave.

The autoclave was heated at 170° C. for 8 hours; the pressure initially stabilized at 26 bars and then gradually decreased to 10 bars upon completion of the reaction. The autoclave was cooled to 120° C. and degassed, and then water (30 g) was slowly introduced therein and the autoclave heated for two hours at 140° C., and then for two hours at 150° C., while at the same time distilling the reaction mixture at atmospheric pressure. After treatment as in Example 1, the benzoxazolone was obtained in a Y of 70% and a DC of 96%.

EXAMPLE 5

Example 4 was repeated, but 9.9 g of $Cu_2Cl_2$ (instead of 19.8 g) were utilized; the benzoxazolone was thus obtained in a Y of 70.5% and a DC of 80.5%.

EXAMPLE 6

Ortho-chlorophenol (102.8 g), urea (240 g) and $Cu_2Cl_2$ (7.92 g) were introduced into a 1 liter stainless steel autoclave equipped with stirring means.

The autoclave was sealed and purged with $NH_3$, and $NH_3$ (51 g) was introduced. The autoclave was heated at 170° C. for 8 hours. The pressure initially stabilized at 38 bars (relative pressure) and then gradually decreased to 24 bars upon completion of the reaction. The autoclave was cooled and opened; water (16 g) was added and the resulting mixture was heated, in the ambient air and under atmospheric pressure, at about 135° C. for 4 hours.

Upon completion of this reaction, a 1 N aqueous solution of sulfuric acid (600 cc) was added to the reaction medium. The precipitate was filtered off and drained and benzoxazolone was thus obtained in a DC 99% and a Y of 78.6%.

EXAMPLE 7

Ortho-chlorophenol (12.85 g), Cu$_2$O (0.715 g), urea (9 g) and NH$_3$ (13.6 g) were introduced into a 125 cc autoclave.

The autoclave was heated for 8 hours at 140° C. The initial pressure of 32 bars gradually decreased to 17 bars. The autoclave was cooled to 125° C., water (2 cc) was added, and then, without any distillation, the autoclave was heated to atmospheric pressure for 1 hour at 130° C. and for 2 hours at 150° C.

Utilizing those recovery techniques above outlined, the benzoxazolone was obtained in a Y of 46% and a DC of 95.5%.

EXAMPLE 8

Urea (30 g), ortho-chlorophenol (12.85 g), Cu$_2$Cl$_2$ (0.99 g) and NH$_3$ (0.68 g) were introduced into a 125 cc autoclave.

The autoclave was heated for 8 hours at 170° C. The pressure stabilized at 10 bars and gradually declined to 9 bars. The procedure was then continued exactly as in Example 7 and the benzoxazolone was obtained in a Y of 41.5% and a DC of 89%.

EXAMPLE 9

Ortho-chlorophenol (102.8 g), urea (240 g), Cu$_2$Cl$_2$ (7.92 g) and water (14.4 g) were introduced into a 1 liter autoclave.

The autoclave was purged with nitrogen and heated for 8 hours at 170° C. The pressurized ammonia atmosphere was thus obtained by decomposition of the urea in the presence of water. Such pressure stabilized at 40 bars, and remained constant at this value. The autoclave was cooled, degassed and heated for 2 hours at 130° C. and then for 2 hours at 150° C., while at the same time conducting the distillation at atmospheric pressure.

Utilizing the aforesaid recovery techniques, the benzoxazolone was obtained in a Y of 57.5% and a DC of 95%.

EXAMPLE 10

Ortho-chlorophenol (24 g), urea (28 g), CuCl$_2$ (2.5 g) and NH$_3$ (6.35 g) were introduced into a 140 cc autoclave lined with polytetrafluoroethylene.

The autoclave was sealed and purged with NH$_3$, and heated at 170° C., for 6 hours. The pressure initially stabilized at about 26 bars (relative pressure) and then gradually declined to about 10 bars upon completion of the reaction. The autoclave was cooled to 120° C. and opened and the contents of the autoclave were transferred into a 250 cc round-bottomed flask under atmospheric pressure, the flask being equipped with a distillation system similar to that described in Example 1. Water (3 cc) was added slowly to this flask; the mixture was subsequently heated for 2 hours at 140° C. and then for 2 hours at 150° C., water being added uniformly at the rate of 4.5 cc/hour throughout the distillation. The mixture was again cooled to 120° C., water (80 cc) was added, the mixture was cooled to 20° C., a 6 N aqueous solution of sulfuric acid (15 cc) was added and then ethyl acetate (50 cc) was added. The aqueous phase was separated off by decantation and washed with ethyl acetate. The benzoxazolone was obtained in the organic phase in a Y of 30% and a DC of 80%.

Benzoxazolone was likewise obtained in the presence of FeCl$_2$, NiCl$_2$ and Ni.

EXAMPLE 11

The procedure of Example 10 was repeated, but with the following modifications:

Ortho-chlorophenol (15.8 g), urea (59 g), cuprous chloride (1.23 g) and NH$_3$ (6.35 g) were introduced.

The autoclave was heated for 6 hours at 210° C. The pressure initially stabilized at about 24 bars (relative pressure) and then gradually declined to about 10 bars upon completion of the reaction.

After the mixture had been transferred into the round-bottomed flask under atmospheric pressure, same was heated for 2 hours at 170° C. and then for 2 hours at 190° C. The benzoxazolone was obtained in a Y of 59% and a DC of 98%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of benzoxazolone comprising, in a first step, heating at an elevated temperature a reaction mixture of ortho-chlorophenol and urea under superatmospheric ammonia pressure until the degree of conversion of the ortho-chlorophenol has essentially stabilized, and thence continuing heating the medium of reaction at an elevated temperature in a second step, but under atmospheric pressure.

2. The process as defined by claim 1, wherein the pressure in the first step ranges from 1 to 60 bars.

3. The process as defined by claim 2, wherein the pressure in the first step ranges from 3 to 40 bars.

4. The process as defined by claim 2, wherein the partial pressure of the ammonia comprising the first step superatmospheric pressure is in excess of 50% of the total pressure.

5. The process as defined by claim 4, wherein the said partial pressure of the ammonia is in excess of 90% of the total pressure.

6. The process as defined by claim 1 or 4, wherein the molar ratio of the urea to the ortho-chlorophenol in the first step reaction mixture ranges from 1 to 15.

7. The process as defined by claim 6, wherein said ratio urea/ortho-chlorophenol ranges from 1.2 to 8.

8. The process as defined by claim 6, wherein the reaction mixture is heated in the first step to a temperature ranging from 100° to 250° C.

9. The process as defined by claim 8, wherein the reaction mixture is heated in the first step to a temperature ranging from 140° to 230° C.

10. The process as defined by claim 8, wherein the medium of reaction is heated in the second step to a temperature ranging from 80° to 220° C.

11. The process as defined by claim 10, wherein the medium of reaction is heated in the second step to a temperature ranging from 110° to 190° C.

12. The process as defined by claim 10, wherein the heating of the reaction mixture is conducted in the presence of water, at least in the second heating step.

13. The process as defined by claim 1, wherein the heating of the reaction mixture is conducted in the presence of a metal catalyst.

14. The process as defined by claim 13, wherein the metal catalyst is a copper catalyst.

15. The process as defined by claim 14, wherein the copper catalyst is a cuprous salt.

16. The process as defined by claim 15, wherein the cuprous salt is cuprous chloride.

17. The process as defined by claim 13 or 14, wherein the amount of catalyst in the reaction mixture ranges from 0.5 to 20% by weight, based upon the weight of the ortho-chlorophenol.

18. The process as defined by claim 17, wherein the amount of catalyst ranges from 2 to 10% by weight, based upon the weight of the ortho-chlorophenol.

19. The process as defined by claim 12, wherein both steps are conducted in the presence of water.

20. The process as defined by claim 12, the water comprising less than 20% by weight of the medium of reaction.

21. The process as defined by claim 19, the water comprising less than 20% by weight of the medium of reaction.

22. The process as defined by claim 1, the first step being conducted in an inert solvent.

23. The process as defined by claim 1, the urea in the reaction mixture being prepared in situ, by reaction between $CO_2$ and the ammonia.

24. The process as defined by claim 1, wherein the second step is conducted under conditions of distillation.

25. The process as defined by claim 14, said catalyst being selected from the group consisting of copper metal, copper oxide, and cuprous or cupric halide, sulfate, phosphate, acetate, propionate and acetylacetonate.

26. The process as defined by claim 13, wherein the metal catalyst is an iron or nickel catalyst.

* * * * *